(12) United States Patent
Garrish et al.

(10) Patent No.: US 10,188,539 B2
(45) Date of Patent: Jan. 29, 2019

(54) STABILIZING SYSTEM FOR A KNEE BRACE

(71) Applicant: Spring Loaded Technology Incorporated, Halifax (CA)

(72) Inventors: Robert Garrish, Halifax (CA); Bradley Eric MacKeil, Halifax (CA)

(73) Assignee: SpringLoaded Technology Incorporated, Dartmouth (CA)

( * ) Notice: Subject to any disclaimer, the term of this patent is extended or adjusted under 35 U.S.C. 154(b) by 376 days.

(21) Appl. No.: 14/874,988

(22) Filed: Oct. 5, 2015

(65) Prior Publication Data
US 2017/0095364 A1    Apr. 6, 2017

(51) Int. Cl.
A61F 5/01    (2006.01)
(52) U.S. Cl.
CPC .......... *A61F 5/0125* (2013.01); *A61F 5/0123* (2013.01); *A61F 2005/0137* (2013.01); *A61F 2005/0179* (2013.01)
(58) Field of Classification Search
CPC .. A61F 5/00; A61F 5/01; A61F 5/0102; A61F 5/0123; A61F 5/0125
USPC .............................................. 602/16, 23, 26
See application file for complete search history.

(56) References Cited

U.S. PATENT DOCUMENTS

| 4,433,679 A | 2/1984 | Mauldin et al. |
|---|---|---|
| 4,558,767 A | 12/1985 | Taylor |
| 4,624,246 A | 11/1986 | Ajemian |
| 4,643,176 A | 2/1987 | Mason et al. |
| 4,665,905 A | 5/1987 | Brown |
| 4,751,920 A | 6/1988 | Mauldin et al. |
| 4,821,707 A | 4/1989 | Audette |
| 4,846,842 A | 7/1989 | Connolly et al. |
| 4,928,676 A | 5/1990 | Pansiera |
| 4,938,207 A | 7/1990 | Vargo |
| 4,961,416 A | 10/1990 | Moore et al. |
| 5,013,037 A | 5/1991 | Sterner |
| 5,042,464 A | 8/1991 | Skwor et al. |
| 5,107,824 A | 4/1992 | Rogers et al. |
| 5,261,871 A | 11/1993 | Greenfield |
| 5,376,137 A | 12/1994 | Shorter et al. |
| 5,395,304 A | 3/1995 | Tarr et al. |
| 5,399,149 A | 3/1995 | Frankowiak et al. |

(Continued)

FOREIGN PATENT DOCUMENTS

| CA | 2628759 A1 | 10/2008 |
|---|---|---|
| GB | 2164415 A1 | 3/1986 |

*Primary Examiner* — Keri J Nelson
(74) *Attorney, Agent, or Firm* — Ralph E. Jocke; Walker & Jocke

(57) ABSTRACT

A knee brace for assisting the extension or flexing of a limb comprises substantially rigid upper and lower frames connected by a hinge, the upper frame being secured to the leg by an upper strap. A stabilizing strap for fixing the lower frame to the user's leg comprises an inelastic band, cord or other flexible securing member for circumscribing the user's leg having a fastening element for fixing the securing member in a set position. The securing member is affixed to the arms of the lower frame, slidably extending through at least one strap support provided by at least one of the arms of the lower frame. When the brace is in position on a user's leg the stabilizing strap is able to move through at least one strap support in a generally horizontal direction while supporting the lower frame in the vertical direction.

16 Claims, 4 Drawing Sheets

(56) References Cited

U.S. PATENT DOCUMENTS

| | | |
|---|---|---|
| 5,437,619 A | 8/1995 | Malewicz et al. |
| 5,472,410 A | 12/1995 | Hamersly |
| 5,624,389 A | 4/1997 | Zepf |
| 5,873,847 A | 2/1999 | Bennett et al. |
| 6,001,075 A | 12/1999 | Clemens et al. |
| RE37,209 E | 6/2001 | Hensley et al. |
| 6,245,034 B1 | 6/2001 | Bennett et al. |
| 6,383,156 B1 * | 5/2002 | Enzerink ............... A61F 5/0125 602/16 |
| 6,471,664 B1 | 10/2002 | Campbell et al. |
| 6,527,733 B1 | 3/2003 | Ceriani et al. |
| 6,878,126 B2 | 4/2005 | Nelson et al. |
| 6,890,314 B2 | 5/2005 | Seligman |
| 6,942,629 B2 | 9/2005 | Hepburn et al. |
| 7,083,583 B2 | 8/2006 | Opahle et al. |
| 7,232,972 B1 | 6/2007 | Yang |
| 7,479,122 B2 * | 1/2009 | Ceriani ................ A61F 5/0123 602/16 |
| 7,553,289 B2 | 6/2009 | Cadichon |
| 7,662,119 B2 | 2/2010 | Detoro et al. |
| 7,670,306 B2 | 3/2010 | Nordt, III et al. |
| 7,682,322 B2 | 3/2010 | Engelman |
| 7,682,323 B2 | 3/2010 | Detoro et al. |
| 7,699,797 B2 | 4/2010 | Nordt, III et al. |
| 7,887,500 B2 * | 2/2011 | Nordt, III ................ A61F 5/32 602/20 |
| 7,927,299 B2 | 4/2011 | Krause |
| 7,967,765 B2 * | 6/2011 | Nathanson ............ A61F 5/0123 602/16 |
| 8,216,166 B2 | 7/2012 | Einarsson et al. |
| 8,328,745 B2 | 12/2012 | Einarsson et al. |
| 8,435,197 B2 | 5/2013 | Vollbrecht et al. |
| 8,551,184 B1 | 10/2013 | Herr |
| 2007/0010772 A1 | 1/2007 | Ryan |
| 2009/0018476 A1 | 1/2009 | Cho |
| 2013/0245524 A1 | 9/2013 | Schofield |

* cited by examiner

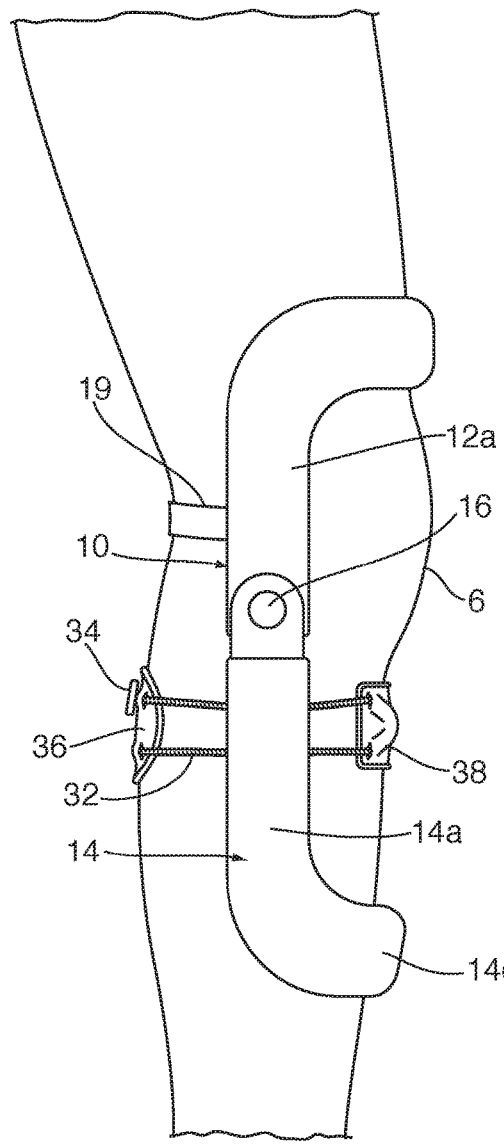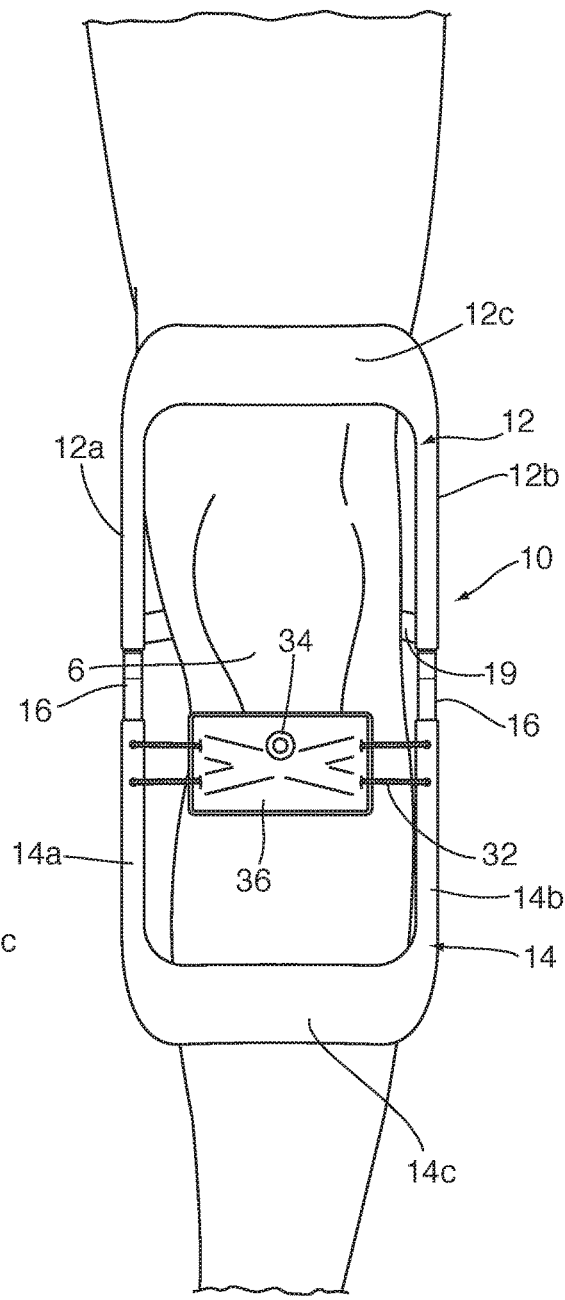
Fig. 9
Fig. 10

STABILIZING SYSTEM FOR A KNEE BRACE

FIELD OF THE INVENTION

This invention relates to braces, and in particular a knee brace for supporting and/or assisting the extension of a user's leg.

BACKGROUND OF THE INVENTION

As is well known, a brace can perform a purely prophylactic function, or provide an assistive force that helps the user to extend their limb, or both. Knee braces in particular can provide physical protection against injury, and may for example be used by athletes involved in high-risk sports where there is a relatively high susceptibility to sustaining a knee injury.

Many individuals suffer from knee problems, often due to a prior knee injury. Some such problems can significantly affect mobility and/or the ability to support the injured person. While corrective measures such as exercise and physiotherapy, or in more serious cases surgery, can assist in correcting or partially alleviating some knee problems, there remains a need in many cases for knee support and extension augmentation.

Particularly where there has been ligament damage, for example a tear or strain in the anterior cruciate ligament (ACL), medial collateral ligament (MCL) or lateral collateral ligament (LCL), a knee brace can be used to both provide support and enhance extension strength, and thus reduce the load on the injured knee. Conventional knee braces that provide active assistance to knee extension are designed to yield when the knee is flexed, loading a torsion spring or compression spring in the process. The spring is loaded when the user bends their leg, and when extending their leg the spring unloads applying a force that augments the extension action. This also helps to support the user and prevent collapse if the injured knee buckles.

A substantial force is required to significantly enhance knee extension and resist buckling of the knee. An example of a knee brace capable of providing the required force is described and illustrated in U.S. patent application Ser. No. 14/526,826 filed Oct. 29, 2014 entitled BRACE AND TENSION SPRINGS FOR A BRACE, which is incorporated herein by reference and referenced by way of non-limiting example only. This brace design provides effective enhancement of the knee extension action in cases where strength enhancement is needed and resistance to buckling of the knee.

However, the forces imparted by the springs in the aforesaid brace create problems with maintaining the correct position of the brace in use. The brace has substantially rigid upper and lower frames which articulate about a joint, typically a polycentric hinge. The upper and lower frames are in turn secured to the leg above and below the knee, respectively, often by straps secured around the leg. Since the ankle cannot be used to support the brace because this would inhibit use of the foot, in a conventional knee brace the strap securing the lower frame to the user's leg is typically secured above the calf (since below the calf the leg tapers in a downward direction). However, because of the large forces involved, even where a strap is secured above the calf over repeated cycles the brace will tend to migrate down the user's leg. This problem is exacerbated by the fact that the cross-sectional shape of the leg changes slightly as the leg moves It would accordingly be advantageous to provide a stabilizing system for a brace that stabilizes the brace in a set position over repeated extension cycles.

BRIEF DESCRIPTION OF THE DRAWINGS

In drawings which illustrate one or more embodiments of the invention by way of example only.

FIG. 9 is a side elevation of a brace according to the invention mounted to a user's leg.

FIG. 10 is a front elevation of the brace of FIG. 9.

DETAILED DESCRIPTION OF THE INVENTION

Figure 1:
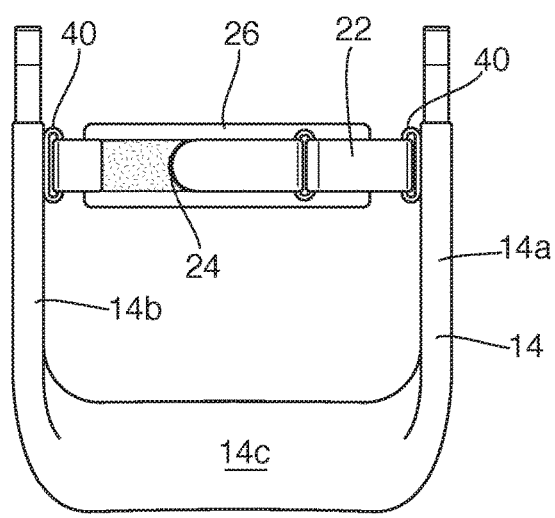
FIG. 1 is a rear elevation of a lower frame of a brace embodying a stabilizing system according to the invention utilizing an inelastic band.
Figure 2:
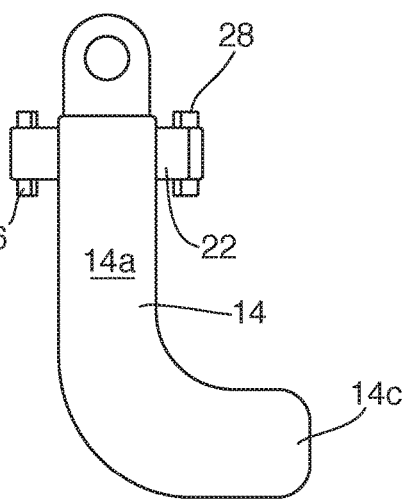
FIG. 2 is a side elevation of the lower frame shown in FIG. 1.
Figure 3:
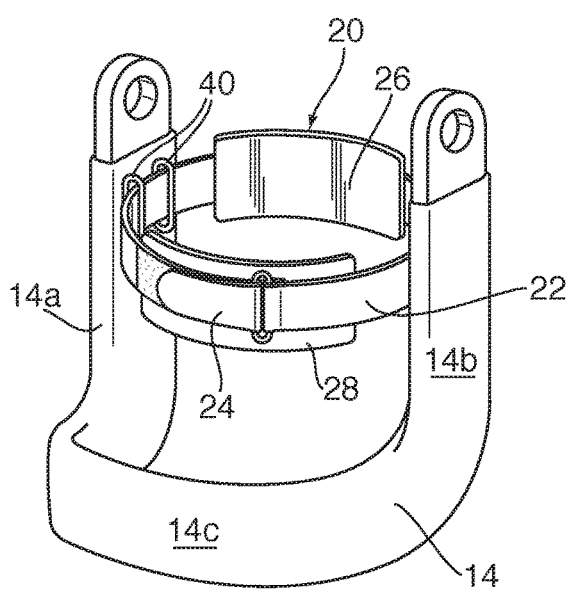
FIG. 3 is a front perspective view of the lower frame shown in FIG. 1.
Figure 4:
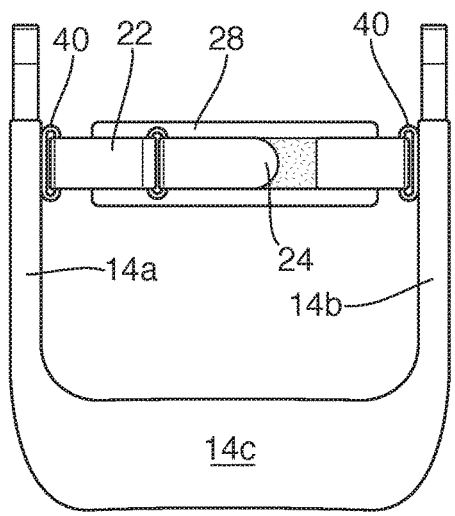
FIG. 4 is a front elevation of the lower frame shown in FIG. 1.
Figure 5:
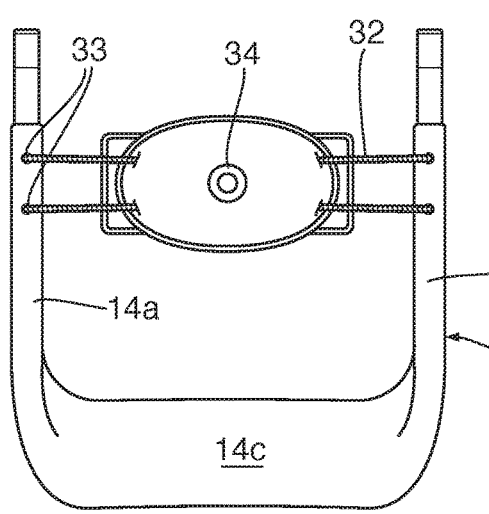
FIG. 5 is a rear elevation of a lower frame of a brace stabilizing system according to the invention utilizing an inelastic cord.
Figure 6:
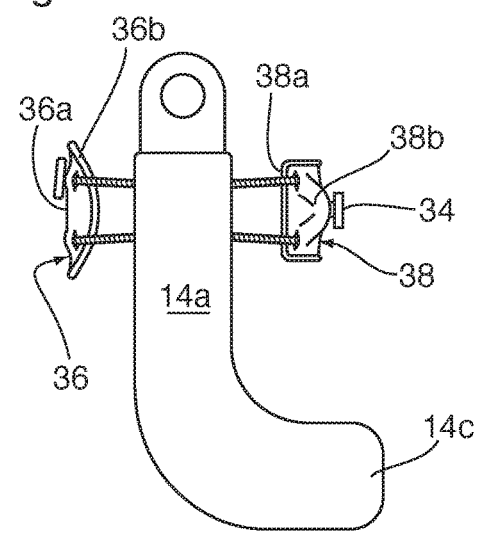
FIG. 6 is a side elevation of the lower frame shown in FIG. 5.

The invention will be described in the context of a knee brace for humans. However, it will be appreciated that the principles of the invention can be applied to braces for other human body appendages and to braces for animals including (without limitation) horses, dogs and cats.

The invention thus provides a knee brace for assisting the extension or flexing of a limb, comprising substantially rigid upper and lower frames connected by a hinge, the upper frame comprising hinge arms each having one end connected to the hinge and an opposite end connected to the other hinge arm by an upper leg bearing member for bearing against a user's leg above the knee, the lower frame comprising hinge arms each having one end connected to the hinge and an opposite end connected to the other hinge arm by a lower leg bearing member for bearing against a user's leg below the knee, at least one upper securing member for fixing the upper frame to the user's leg, and a stabilizing strap for fixing the lower frame to the user's leg, comprising an inelastic element for circumscribing the user's leg having a fixing element for securing the band in a set position, the band slidably extending through at least one strap support provided by at least one of the arms of the lower frame and being affixed to the other of the arms of the lower frame, such that when the brace is in position the stabilizing strap is able to move through the at least one strap support in a generally horizontal direction while supporting the lower frame in the vertical direction.

The invention further provides, for a knee brace for assisting the extension or flexing of a limb, the knee brace comprising substantially rigid upper and lower frames connected by a hinge, the upper frame comprising hinge arms each having one end connected to the hinge and an opposite end connected to the other hinge arm by an upper leg bearing member for bearing against a user's leg above the knee, the lower frame comprising hinge arms each having one end connected to the hinge and an opposite end connected to the other hinge arm by a lower leg bearing member for bearing against a user's leg below the knee, and at least one upper securing member for fixing the upper frame to the user's leg, a stabilizing system comprising: a stabilizing strap for fixing the lower frame to the user's leg, comprising an inelastic element for circumscribing the user's leg having a fixing element for securing the band in a set position, the band slidably extending through at least one strap support provided by at least one of the arms of the lower frame and being affixed to the other of the arms of the lower frame, such that when the brace is in position the stabilizing strap is able to move through the at least one strap support in a generally horizontal direction while supporting the lower frame in the vertical direction.

In the illustrated example of a brace 10 according to the invention, a lower frame 14 is pivotally connected to an upper frame 12 as hinge 16, so that the upper and lower frames 12, 14 can pivot relative to each other. As shown in FIGS. 9 and 10, when the knee brace is in position the pivots 16 are respectively disposed on either side of the leg along the axis of rotation of the knee 6, and the frames 12, 14 thus freely pivot relative to one another as the knee 6 flexes and extends. In other embodiments the frames 12, 14 may be geared to each other, or otherwise coupled by a linkage such that they rotate in synchronization.

The knee brace 10 illustrated applies a force to assist the user in extending the knee 6 when the knee 6 has been flexed. This restoring force is supplied by a loading system 18, which can be any suitable loading system including (without limitation) the tension springs described and illustrated in U.S. patent application Ser. No. 14/526,826, which is incorporated herein by reference.

According to the invention, a securing system for a brace 10 comprises a single stabilizing strap 20 affixed to the lower frame 14 of the brace 10 in the manner hereinafter described, which circumscribes the entire circumference of the lower leg at a position between the bottom of the knee 6 and top of the calf muscle. When adjusted the stabilizing strap 20 uniformly tightens around the leg, providing a secure fit.

In the embodiment illustrated the knee brace comprises a substantially rigid upper frame 12 and a substantially rigid lower frame 14 connected by opposed hinges 16. The frame portions 12, 14 may be formed from metal, plastic, fiberglass or any other relatively rigid material which is preferably lightweight, durable and capable of withstanding the elements (for wearing in inclement weather).

The upper frame 12 comprises hinge arms 12a, 12b each having one end connected to the hinge 16 and an opposite end connected to the other hinge arm by an upper leg bearing member 12c for bearing against a user's leg above the knee 6. The lower frame 14 similarly comprises hinge arms 14a, 14b each having one end connected to the hinge 16 and an opposite end connected to the other lower frame hinge arm by a lower leg bearing member 14c for bearing against a user's leg below the knee.

The upper frame 12 is fixed to the user's leg by an upper securing member, as shown an upper strap 19, located so as to bear against the leg above the knee 6. The upper strap 19 serves to hold the leg bearing member 12c securely against the user's quadriceps, so that when the leg is bent the brace 10 bends along with the leg at hinges 16.

The lower frame 14 is fixed to the user's leg by a stabilizing strap comprising a flexible, substantially non-stretchable securing member. In the embodiment illustrated in FIGS. 1 to 4 the securing member comprises an inelastic tensioning band 22, for example made from nylon or another substantially non-stretchable material, for circumscribing the user's leg. The band 22 comprises a releasable fixing element 24 for securing the band 22 in a desired position at a selected tension, in the embodiment illustrated a hook-and-loop fastener such as Velcro (Trademark). Other fasteners capable of retaining the band 22 in with a set circumference, including without limitation hook-and-eye fasteners, grapple grommets, toggle levers and lacing, may also be used. For convenience and ease of use, fasteners that are easy to fasten and do not change the selected circumference of the band 22 when fastened are preferred.

The band 22 is affixed to the arms 14a, 14b of the lower frame 14. The band 22 slidably extends through at least one arm 14a, 14b, for example through one or more strap supports 40 projecting from, affixed to or otherwise provided by at least one arm 14a, 14b.

In the embodiments shown in FIGS. 1 to 4 the strap supports comprise at least one strap retaining member 40, such as a steel ring or bight that traps the strap 22 in horizontally slidable relation, affixed to the interior surface of each arm 14a, 14b at any desired position along the arms 14a, 14b. Thus, when the brace 10 is in position on the user's leg the stabilizing strap 20 is movable through the strap supports 40 in a generally horizontal direction but not in a vertical direction, to thereby support the lower frame in the vertical direction while 'floating' in the horizontal direction. The strap supports 40 may be formed from any suitable material and affixed to or integrated into the lower frame 14 in any suitable fashion. For example, the strap supports 40 may be fixed to a plastic or rubberized backer that is in turn fixed to the lower frame 14 with a single point of contact (for example riveted).

Figure 11:
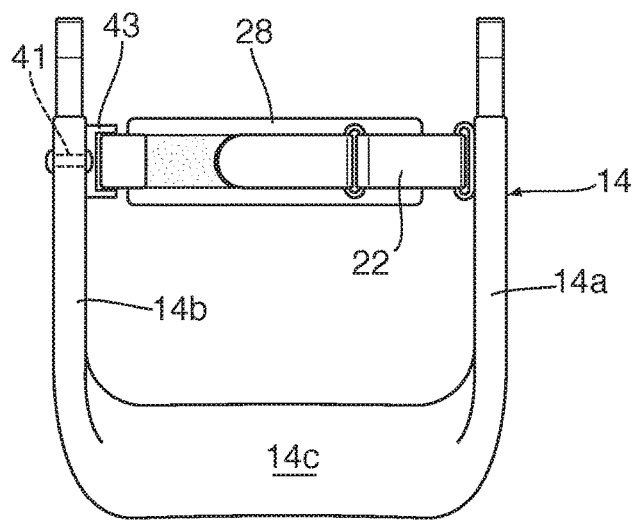
FIG. 11 is a rear elevation of the lower frame of a brace employing a further embodiment of a stabilizing system according to the invention.
Figure 12:
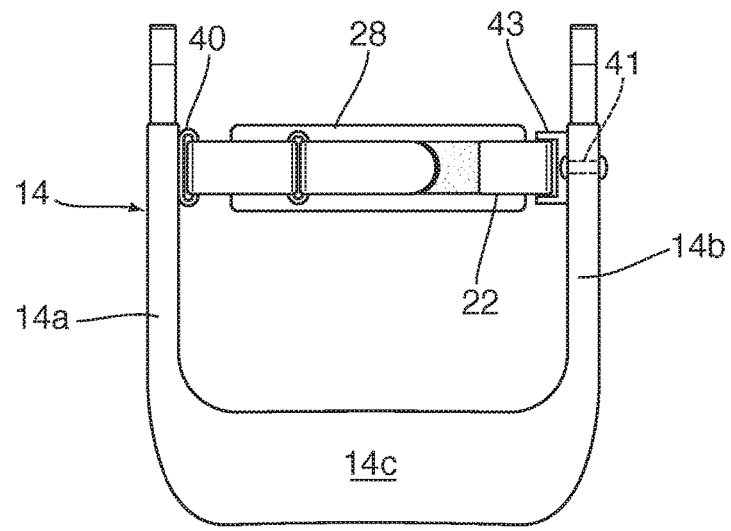
FIG. 12 is a front elevation of the lower frame shown in FIG. 11.

In the embodiment shown in FIGS. 11 and 12 at least one strap retaining member 40 such as a steel ring or bight is affixed to the interior surface of one arm, 14a in the embodiment shown, at the desired position; and the strap 22 is fixed to the other arm, 14b in the embodiment shown, in both horizontally and vertically fixed relation, for example by a bolt, rivet or any other suitable fastener 41 affixing the strap 22 directly to the arm 14b. Alternatively, the fastener may include a quick-connect coupler such as a luggage strap connector 43 as shown, one end of which is fixed to the arm 14b (also by a bolt, rivet or any other suitable fastener), for ease of attaching the brace 10 to the user's leg. Thus, when the brace 10 is in position on the user's leg the stabilizing strap 20 is movable through the strap support 40 on one arm (e.g. 14a) in a generally horizontal direction but not in a vertical direction, to thereby support the lower frame in the vertical direction while 'floating' in the horizontal direction, while the stabilizing strap 20 is fixed by fastener to the other arm (e.g. 14b) to prevent the strap 22 from moving in any direction relative to the arm 14b. This provides essentially the same ability, overall, for the strap 22 to 'float' in the horizontal direction. The stabilizing strap 20 comprises a rear shell 26 which partially or fully overlies the calf muscle, for load bearing purposes. The band 22 is fixed to (or around) the exterior surface of the shell 26, which may be formed from carbon-fibre so as to be durable and semi-rigid, but is preferably formed thin enough to be flexible so as to largely yield to the shape of the calf for stability and comfort. If the band 22 is not sufficiently comfortable by itself, the stabilizing strap 20 may optionally further comprise a front pad 28 for comfort, which can also be formed from carbon-fibre or may comprise a flexible cushioning pad that spreads the load of the tightened band 22 over a larger portion of the user's shin.

In a conventional brace the securing strap is tightened against the brace frame, rather than solely against the leg. This can leads to the strap being over-tight on one of the front or back of the frame and too loose on the other, which in turn can lead to brace migration and discomfort. Even when a strap is properly tensioned against the brace frame in a static position, as the leg changes shape and position during motion the strap can migrate into a different position. When a stabilizing strap 20 according to the invention is mounted to the lower frame 14, tensioning the stabilizing strap 20 loads the front and back of the band 22 against each other, this constricting the strap 22 only against the user's leg, rather than loading the strap 22 against the lower frame 14. The resulting freedom of motion in a horizontal plane allows for more precise tightening of the stabilizing strap 20 for both effectiveness and comfort, and allows the stabilizing strap 20 to follow leg's motion and changes in shape as it is bent without shifting the position of the brace 10.

A brace 10 according to the invention is thus designed to securely grasp a users' lower leg and restrict vertical brace migration. Allowing the stabilizing strap 20 to move through supports 40 on (or integrated into) the lower frame 14 in a horizontal plane facilitates a uniform pressure of the stabilizing strap 20 around the leg for a secure fit, securely clinching the leg and restricting the motion of the strap in a vertical direction to eliminate vertical brace migration.

In use, the brace 10 is placed over the user's leg at the correct position with the hinge 16 in alignment with the knee 6, and the upper frame 12 is secured above the knee. The rear shell 26 is positioned over the rear of the leg, overlapping the calf muscle partially or fully, and the front pad 28 is centred over the user's shin. The tensioning band 22 is tightened to the desired loading and the fastener 38 is engaged to fix the stabilizing strap 20 in position. The stabilizing strap 20 then supports the brace 10 vertically, to maintain the desired vertical positioning, but is able to move in a horizontal plane and thus accommodate the changing shape and exterior profile of the leg when the user is in motion.

A further embodiment of the invention is illustrated in FIGS. 5 to 10. In this embodiment the stabilizing strap 30 comprises a rear shell 36 which partially or fully overlies the calf muscle for load bearing purposes, and may further comprise a front pad 38 for comfort, as described above in relation to the previous embodiment. The flexible tensioning member in this embodiment comprises at least one inelastic tensioning cord 32, for example made from nylon lacing or another substantially non-stretchable material, for circumscribing the user's leg.

In this embodiment the strap supports through which the cord 32 slidably extends comprise holes 33 disposed transversely through the lower frame 14 so that, as in the previous embodiment, the tensioning member 32 'floats' in a horizontal plane and can thus move independently of the lower frame 14 in a horizontal plane while supporting the lower frame 14 vertically.

The cord 32 is affixed to, around or through the front pad 38, preferably in slidable relation so that the front pad 38 is able to move relative to the cord 32 and can thus always be positioned over the shin centrally between the arms 14a, 14b, regardless of the size of the user's leg or the amount of tension applied to the cord 32.

Figure 7:
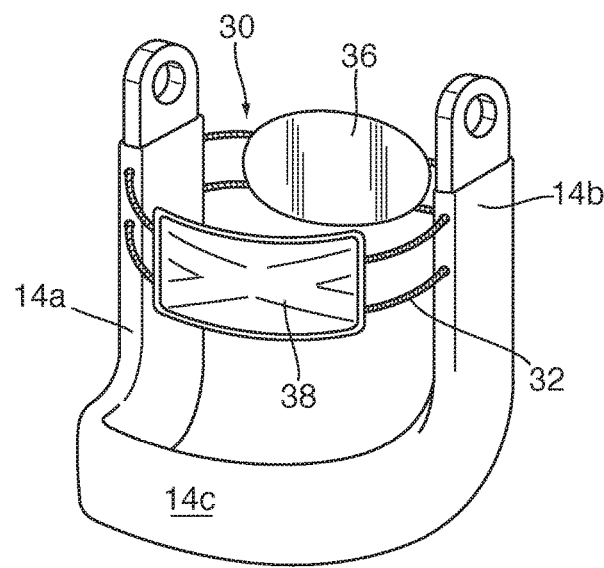
FIG. 7 is a front perspective view of the lower frame shown in FIG. 5.
Figure 8:
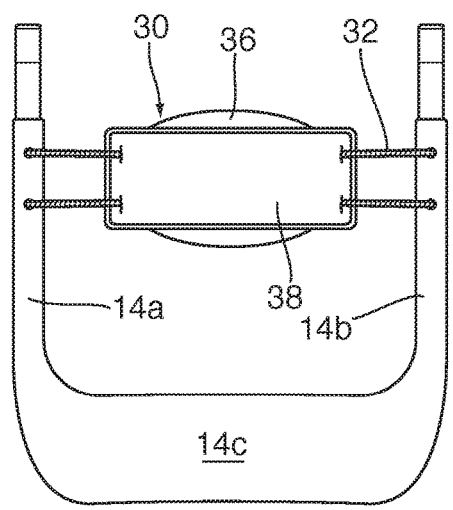
FIG. 8 is a front elevation of the lower frame shown in FIG. 5.

The cord 32 is also affixed to, around or through the rear shell 36. In the embodiment illustrated a single piece of lace or other material is used for the tensioning cord 32, doubled so as to circumscribe the user's leg twice when in use. As best seen in FIG. 7 the cord 32 is disposed through the front pad 38, extending through holes in a rigid or semi-rigid backing layer 38b and thus slidably received between an inner cushioning layer 38a and the backing layer 38b. Since a single cord 32 is used in this embodiment, the cord 32 crosses over itself within the front pad 38 so that the two circumscribing portions of the cord 32 can be spaced apart, preferably disposed near top and bottom edges of the front pad 38 and rear shell 36 to distribute the loading force.

In this embodiment the rear shell 36 comprises a tightening knob 34, for example affixed to the rear shell 36 around which the cord 32 is wound such that rotating the knob 34 tightens or loosens the tension on the cord 32, allowing for a proper fit regardless where the lower frame 14 sits on the leg and to accommodate legs of different sizes. The tightening knob 34 actuates a reel (not shown) embedded in the rear shell 36, that the cord 32 winds onto or pays off from, which tightens the upper circumscribing portion of the cord 32 as the user bends their leg. The cord 32 naturally slides through the lower frame 14 and front pad 38 to equalize the tension. The knob may be affixed to the reel by a releasable ratchet or other mechanism which maintains tension on the cord 32 until released by the user. Thus, when the knob 34 is rotated to tighten the cord 32 the shell 36 and front pad 38 securely clinch the lower leg.

The embodiment in which the securing member is horizontally slidable relative to one of the lower arms 14a, 14b and horizontally fixed relative to the other of the lower arms 14a, 14b also applies to embodiments utilizing an inelastic cord 32 or other securing member. In the case of a cord 32, the cord 32 can be horizontally fixed to the other of the arms 14a, 14b in any suitable fashion, including for example by forming a male or female coupler component in the arm itself; by filling the hole 33 with epoxy or another curable compound or adhesive; by fitting a plug or screw into the hole 33; by knotting the cord on either side of the arm; or in any other suitable fashion.

Various embodiments of the present invention having been thus described in detail by way of example, it will be apparent to those skilled in the art that variations and modifications may be made without departing from the invention. The invention includes all such variations and modifications as fall within the scope of the appended claims.

The invention claimed is:

1. A knee brace for assisting the extension or flexing of a limb, comprising substantially rigid upper and lower frames connected by a hinge, the upper frame comprising hinge arms each having one end connected to the hinge and an opposite end connected to the other hinge arm by an upper leg bearing member for bearing against a user's leg above the knee, the lower frame comprising first and second hinge arms extending in a first direction and each having one end connected to the hinge and an opposite end connected to the other hinge arm by a lower leg bearing member for bearing against the user's leg below the knee, a first strap support being provided on the first hinge arm and an opposing second strap support being provided on the second hinge arm, at least one upper securing member for fixing the upper frame to the user's leg, and a stabilizing strap for fixing the lower frame to the user's leg, the stabilizing strap comprising a substantially inelastic element for circumscribing the user's leg and a fixing element for securing the inelastic element in a set position, the inelastic element extending through the first and second strap supports, such that when the brace is in use the stabilizing strap is inhibited from moving relative to the lower frame in the first direction to support the lower frame on the user's leg and is slidable relative to the lower frame in a second direction that is orthogonal to the first direction, wherein when the knee brace is in use the stabilizing strap follows the user's leg motion in the second direction without shifting the lower frame relative to the user's leg in the first direction.

2. The knee brace of claim 1 wherein the inelastic element comprises a band.

3. The knee brace of claim 2 wherein the first strap support comprises a ring or bight through which the inelastic element is slidably received.

4. The knee brace of claim 3 wherein the second strap is affixed in a fixed relation relative to the second hinge arm.

5. The knee brace of claim 4 wherein the second strap support comprises a quick-connect coupler.

6. The knee brace of claim 1 wherein the inelastic element comprises a cord.

7. The knee brace of claim 6 wherein the first strap support comprises an opening through one of the first hinge arm through which the cord slidably extends.

8. The knee brace of claim 7 wherein the strap support affixed to the other of the arms of the lower frame is affixed in fixed relation.

9. A stabilizing system for a knee brace, having a substantially rigid upper frame comprising hinge arms each having one end connected to the hinge and an opposite end connected to the other hinge arm by an upper leg bearing member for bearing against a user's leg above the knee and being securable to the user's leg via at least one upper securing member, and a substantially rigid lower frame comprising first and second hinge arms each having one end connected to the upper frame via a hinge and an opposite end connected to the other hinge arm by a lower leg bearing member for bearing against the user's leg below the knee the stabilizing system comprising:

a stabilizing strap for fixing the lower frame to the user's leg, the stabilizing strap comprising a substantially inelastic element for circumscribing the user's leg and having a fixing element for securing the inelastic element in a set position, the inelastic element extending through the first and second strap supports, such that when the brace is in use the stabilizing strap is inhibited from moving relative to the lower frame in the first direction to support the lower frame on the user's leg and is slidable relative to the lower frame in a second direction that is orthogonal to the first direction, wherein when the knee brace is in use the stabilizing strap follows the user's leg motion in the second direction without shifting the lower frame relative to the user's leg in the first direction.

10. The stabilizing system of claim 9 wherein the inelastic element comprises a band.

11. The stabilizing system of claim 10 wherein the first strap support comprises a ring or bight through which the band is slidably received.

12. The stabilizing system of claim 11 wherein the second strap support is affixed in fixed relation relative to the second hinge arm.

13. The stabilizing system of claim 12 wherein the second strap support comprises a quick-connect coupler.

14. The stabilizing system of claim 9 wherein the inelastic element comprises a cord.

15. The stabilizing system of claim 14 wherein the first strap support comprises an opening through the first hinge arm through which the cord slidably extends.

16. The stabilizing system of claim 15 wherein the second strap support is affixed in fixed relation relative to the second hinge arm.

\* \* \* \* \*